United States Patent [19]

Hatfield

[11] 4,044,002

[45] Aug. 23, 1977

[54] REDUCTION PROCESS FOR CEPHALOSPORIN SULFOXIDES

[75] Inventor: Lowell D. Hatfield, Bargersville, Ind.

[73] Assignee: Eli Lilly and Company, Indianapolis, Ind.

[21] Appl. No.: 694,516

[22] Filed: June 9, 1976

[51] Int. Cl.$^2$ .......................................... C07D 501/04
[52] U.S. Cl. .................................... 544/16; 424/246; 544/21; 544/24; 544/25; 544/26; 544/27; 544/28; 544/29; 544/30; 544/22
[58] Field of Search .................................... 260/243 C

[56] References Cited

U.S. PATENT DOCUMENTS 3,641,014  2/1972  Murphy et al. .................. 260/243 C Primary Examiner—Nicholas S. Rizzo
Attorney, Agent, or Firm—William B. Scanlon; Everet F. Smith

[57] ABSTRACT

Cephalosporin sulfoxides are reduced to the corresponding cephalosporin with acyl bromides, e.g., acetyl bromide, in the presence of a bromine scavenger, e.g., an olefin, acetylene, phenol, phenol ether, or an organophosphite. For example, p-nitrobenzyl 7-phenoxyacetamido-3-methyl-3-cephem-4-carboxylate sulfoxide is reduced with acetyl bromide in the presence of amylene to p-nitrobenzyl 7-phenoxyacetamido-3-methyl-3-cephem-4-carboxylate.

23 Claims, No Drawings

REDUCTION PROCESS FOR CEPHALOSPORIN SULFOXIDES

BACKGROUND OF THE INVENTION

Cephalosporin sulfoxides are widely used intermediates in the synthesis of cephalosporin antibiotics. For example, cephalosporin sulfoxides are useful in the overall process for converting 3-methyl-3-cephem(desacetoxycephalosporins) compounds to 3-substituted-methyl-3-cephem antibiotic compounds. This functionalization of 3-methyl-3-cephem compounds proceeds via the isomerization of the 3-methyl-3-cephem to a 3-methyl-2-cephem, functionalization of the activated 3-methyl group of the 2-cephem compound, for example, with bromine, followed by oxidation of the 3-substituted-methyl-2-cephem compound to the sulfoxide. Oxidation to the sulfoxide causes the isomerization of the 2-cephem to the 3-cephem product. The isomerization of 3-halomethyl-2-cephem compounds to the corresponding 3-halomethyl-3-cephem compounds is described by Murphy in U.S. Pat. No. 3,705,897. Further examples of this use of sulfoxides in converting 2-cephem compounds to 3-cephem compounds are described by Cooper in U.S. Pat. No. 3,647,786, and by Webber in U.S. Pat. Nos. 3,766,177, 3,637,678, and 3,708,479.

Additional examples of uses of cephalosporin sulfoxides are the N-deformylation procedure of 7-β-formamido-3-halomethyl-3-cephem sulfoxides described by Humber in U.S. Pat. No. 3,716,533, the 3-formyl-3-cephem sulfoxides described by Webber in U.S. Pat. No. 3,674,784 and the 7-(D-2,2-dimethyl-3-nitroso-5-oxo-4-phenyl-1 -imidazolidinyl)-3-bromomethyl-3-cephem-4-carboxylic acid sulfoxides described by Chaney et al. in U.S. Pat. No. 3,767,655.

Still further examples of the use of cephalosporin sufloxides in the synethesis of cephalosporin antibiotics are the 7-acylamido-2-spirocyclopropyl cephalosporin sulfoxides described by Spry in U.S. Pat. No. 3,843,640, the 2-methylene and 2-methyl substituted cephalosporin sulfoxides described by Wright in U.S. Pat. No. 3,660,396 and the tricyclic cephalosporin sulfoxides described by Spry in U.S. Pat. No. 3,907,785. The preparation of 3-exomethylenecepham sulfoxides via azetidinone sulfinyl chlorides and Lewis acid type Friedel-Crafts catalyst is described by Kukolja in copending application Ser. No. 673,036 filed Apr. 2, 1976. These 3-exomethylenecepham sulfoxides are useful intermediates in the preparation of the 3-halo substituted cephalosporins described by Chauvette in U.S. Pat. No. 3,925,372 and in the synthesis of 3-methoxy-3-cephem antibiotic compounds described by Chauvette in U.S. Pat. Nos. 3,917,587 and 3,917,588. For example, an ester of a 3-exomethylenecepham sulfoxide is reduced to the corresponding 3-exomethylenecepham ester, the ester is then reacted with ozone to form the corresponding 3-hydroxy-3-cephem ester, and the 3-hydroxy ester is reacted with phosphorous trichloride to form the corresponding 3-chloro-3-cephem ester. Alternatively, the 3-hydroxy ester is reacted with diazomethane to form the corresponding 3-methoxy-3-cephem ester. Deesterification of the 3-halo and 3-methoxy esters, affords corresponding 3-halo or 3-methoxy-substituted antibiotic acid.

As noted above, cephalosporin sulfoxides are generally useful in the synthesis of cephalosporin antibiotics. Following the completion of the reactions or synthetic procedures employing the sulfoxide form of a cephalosporin, the sulfoxide function is reduced to provide the cephalosporin molecule in the reduced or sulfide state. Prior to this invention, the preferred method for reducing cephalosporin sulfoxides was that of Murphy et al., U.S. Pat. No. 3,641,014. According to this method, cephalosporin sulfoxides are reduced with 1) hydrogen and a hydrogenation catalyst, 2) stannous, ferrous, cuprous, or manganous cations, 3) dithionite, iodide, or ferrocyanide, 4) trivalent phosphorous compounds, 5) halosilanes or 6) chloromethylene iminium chlorides wherein certain of these reducing agents require the use of an activator such as acetyl chloride or phosphorous trichloride. For example, sodium dithionate is activated with acetyl chloride in the reduction.

In view of the usefulness of cephalosporin sulfoxides in the synthesis of cephalosporin antibiotics, an alternative and more efficient method for the reduction of cephalosporin sulfoxides would be desirable. It is an object of this invention to provide a process for the reduction of cephalosporin sulfoxides.

Summary of the Invention

According to the process of this invention, a cephalosporin sulfoxide as the free acid or as an ester thereof is reacted in an inert solvent with between 2 and 3 moles of an acyl bromide in the presence of a bromine scavenger to provide the corresponding cephalosporin free acid or ester. The reaction can be carried out at a temperature between about $-25°$ and $50°$ C. and preferably between about $0°$ and about $25°$ C. Acyl bromides which can be employed in the process include the lower alkyl carboxylic acid bromides such as acetyl bromide and butyryl bromide and the substituted lower alkyl carboxylic acid bromides wherein the alkyl portion can be substituted with halogen, cyano, or esterified carboxyl groups; the cycloalkyl carboxylic acid bromides such as cyclohexane carboxylic acid bromide and cyclopentane carboxylic acid bromide; the aromatic carboxylic acid bromides such as benzoyl bromide and the substituted benzoyl bromide wherein the phenyl ring can be substituted with lower alkyl, lower alkoxy, halogen, or nitro; or the acyl bromide can be a naphthoic acid bromide.

Bromine scavengers which can be employed in the process of this invention include olefins, acetylenes, dienes, cycloalkenes, or bicycloalkenes; or organophosphites such as the triarylphosphites for example, triphenylphosphite; the trialkylphosphites, for example, triethylphosphite; or mixed aryl alkylphosphites such as diethyl phenylphosphite; or the bromine scavenger can be a readily brominated aromatic compound such as phenol and substituted phenol, for example, the cresols; phenol ethers such as anisol, phenetole, m-dimethoxybenzene, and guiacol.

The preferred acyl bromide in the process of this invention is acetyl bromide and the preferred bromine scavenger is a $C_2$ to $C_5$ alkene, for example, ethylene, propylene, butylene or amylene.

The reduced cephalosporin free acid or ester obtained in the process of this invention with the corresponding sulfoxide can be recovered from the reduction mixture by employing the usual methods employed in the cephalosporin art.

DETAILED DESCRIPTION OF THE INVENTION

According to the process of this invention, cephalosporin sulfoxides are reduced with acyl bromides in the presence of a bromine scavenger to the corresponding cephalosporin. The process is illustrated by the following generalized reaction scheme:

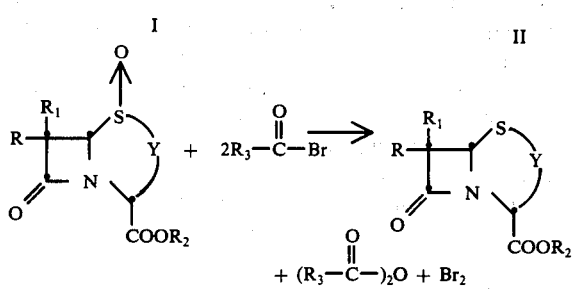

In the above formulas, R represents a substituted amino group, $R_1$ represents hydrogen, a lower alkyl group, or a lower alkoxy group, $R_2$ represents hydrogen, or a carboxylic acid protecting group, and Y represents the structural moiety (a) or the structural moiety (b) represented by the formulas:

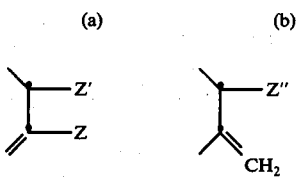

wherein Z, Z', and Z" represent hydrogen or a substituent group. $R_3$ in the above reaction scheme represents the organic residue of the carboxylic acid bromide.

The sulfoxide reduction process of this invention can be carried out on any cephalosporin sulfoxide. As discussed above, numerous cephalosporin sulfoxides have been described and are commonly employed intermediates in the synthesis of cephalosporin antibiotics.

As used herein, the term "cephalosporin sulfoxide" refers to the bicyclic compounds having a 4-membered β-lactam ring fused to a 6-membered thiazine or a dihydrothiazine ring as represented by the above formula I. When in the above formula I Y is the structural moiety (a), the cephalosporin sulfoxide is alternatively named according to the cepham nomenclature system as a 3-cephem sulfoxide. Likewise, when Y is the structural moiety (b), the cephalosporin sulfoxide is named as a cepham sulfoxide and in particular a 3-exomethylenecepham sulfoxide.

In the above formula I the substituted amino group R is in the β-configuration while the group $R_1$ is in the α-configuration. For example, R represents an acylamino group such as the 7β-phenoxyacetylamino group and $R_1$ can be the 7α-methoxy group.

The terms Z, Z', and Z" in the formula I represent hydrogen or substituent groups of known cephalosporin compounds, for example, those groups forming substituents present in the known cephalosporins described in the above-cited art. For example, Z can be hydrogen, methyl, acetoxymethyl, bromomethyl, formyl, vinyl, ethoxycarbonylvinyl, methoxymethyl, or methylthiomethyl. Z' and Z" can be, for example, hydrogen, methyl, an exomethylene group or a spirocyclopropyl group.

The cephalosporin sulfoxide used in the process of this invention can have either the α or the β configuration. In the above reaction scheme, the arrow employed to designate the bonding between the sulfur and oxygen atom of the sulfoxide group is employed herein to designate either configuration.

Preferably the cephalosporin sulfoxide is free of reactive functional groups, such as the unsubstituted or free amino group, which are capable of being acylated with the acyl bromide during the process. Such acylatable groups as the amino group, however, can be protected or blocked during the reduction to prevent their acylation.

The process of this invention is carried out by reacting the cephalosporin sulfoxide either as the free acid or as an ester in an inert solvent with at least 2 moles of an acyl bromide per mole of sulfoxide. As the reduction proceeds bromine is produced as a side product, and in order to prevent the production of undesirable side products which may be formed by the reaction of the bromine with the cephalosporin product, a bromine "scavenger" is used in the reaction mixture to react with or inactivate the bromine as it is formed.

The temperature at which the process can be carried out is not critical, for example, the reduction of the sulfoxide can be carried out at a temperature between about −25° C. and about 50° C. Preferably the reaction is carried out at the convenient temperatures of between about 0° and about 30° C.

Although as indicated by the above reaction scheme, at least 2 molar equivalents of the acyl bromide are required for complete reduction, it is preferable to employ between 2 and 3 moles of the acyl bromide per mole of the cephalosporin sulfoxide. The process is preferably carried out under substantially anhydrous conditions; however, it is unnecessary to maintain the reaction mixture scrupulously dry as minor amounts of water are well tolerated.

As mentioned above, the sulfoxide reduction is carried out in an inert solvent. The term "inert solvent" as used herein refers to organic solvents in which the cephalosporin sulfoxide is at least partially soluble and which do not participate in the reaction, e.g., by reacting with the acyl bromide in competition with the cephalosporin sulfoxide. A wide choice of organic solvents are available for use in the process of this invention. Solvents which can be employed include the chlorinated hydrocarbon solvents such as methylene chloride, chloroform, dichloroethane, trichloroethane, and the like; the organonitriles for example, acetonitrile, propionitrile, butyronitrile, and the like; ether solvents, for example, tetrahydrofuran, dioxane, the dimethyl ether of ethylene glycol, diethyl ether, dibutyl ether, and the like; ketones, for example, acetone, methyl ether ketone, diethyl ketone, and the like; esters, for example, those formed with the lower alkanols and lower carboxylic acids, for example, ethyl acetate, methyl acetate, isoamyl acetate, methyl butyrate, ethyl propionate, and the like. The amide solvents which are commonly used in organic chemistry, for example, dimethylformamide and dimethylacetamide can also be employed in the process of this invention either as the solvent or as a cosolvent with any of the solvents previously mentioned. Mixtures of solvents can likewise be employed in the process.

The reducing agent employed in the process of this invention is a carboxylic acid bromide represented by the formula, $R_3C(O)Br$. A wide variety of carboxylic acid bromides can be used as reducing agents in the process of this invention, for example $R_3$ can represent a $C_1-C_{10}$ alkyl group which may be substituted with substituent groups which are inert under the process conditions, for example, the substituent group can be a halogen atom, for example, fluoro, chloro, or bromo, a cyano group, $C_1-C_4$ alkoxycarbonyl (an esterified carboxy group), a $C_1-C_4$ alkoxy group, or a phenyl group. Examples of such alkyl carboxylic acid bromides include, for example, acetyl bromide, propionyl bromide, n-butyryl bromide, iso-butyryl bromide, n-valeryl bromide, iso-valeryl bromide, n-caproyl bromide, n-heptanoyl bromide, n-capryl bromide, n-octanoyl bromide, iso-octanoyl bromide, n-nonanoyl bromide, n-decanoyl bromide, and like alkyl carboxylic acid bromides. Examples of substituted alkyl carboxylic acid bromides which can be used in the process include, for example, bromoacetyl bromide, cyanoacetyl bromide, 2-chloropropionyl bromide, methoxyacetyl bromide, ethyl malonyl bromide, phenylacetyl bromide, 3-phenylbutyryl bromide, 4-chlorobutyryl bromide, 4-cyanobutyryl bromide, ethyl succinoyl bromide, ethyl glutaryl bromide, and like halo, cyano, phenyl, and esterified carboxy-substituted alkyl carboxylic acid bromides.

Cycloalkyl carboxylic acid bromides can also be employed as reducing agents in the process of this invention. Accordingly, the group $R_3$ can represent a cycloalkyl residue wherein the cyclo ring contains between 3 and 8 ring carbon atoms, for example, $R_3$ can represent cyclopropyl, cyclobutyl, cyclopentyl, cyclohexyl, cycloheptyl, or cyclooctyl. Illustrative of the acid bromides of cycloalkyl carboxylic acids which can be used include the acid bromides of cyclopropane carboxylic acid, cyclobutane carboxylic acid, cyclopentane carboxylic acid, cyclohexane carboxylic acid, cycloheptane carboxylic acid, and cyclooctane carboxylic acid.

The acyl bromide can likewise be an aromatic carboxylic acid bromide wherein $R_3$ represents phenyl or phenyl optionally substituted with one or more of the substituent groups such as fluoro, chloro, bromo, cyano, nitro, lower alkyl, for example, methyl or ethyl, lower alkoxy, for example, methoxy or ethoxy, or esterified carboxy. Examples of aromatic carboxylic acid bromides which can be used are benzoyl bromide, the toluic acid bromides, 4-chlorobenzoyl bromide, 3-bromobenzoyl bromide, 4-nitrobenzoyl bromide, 3-cyanobenzoyl bromide, 3-chloro-4-methylbenzoyl bromide, 3,4-dimethoxybenzoyl bromide, the acid bromide of terephthalic acid mono ethyl ester, and like benzoyl bromides.

The acid bromides of dicarboxylic acids can also be used as reducing agents in the process. For example, the acid bromides of malonic acid, succinic acid, glutaric acid, adipic acid, pimelic acid, and the like, can be used. When a diacyl bromide is employed as reducing agent, it will be recognized that one can employ at least 1 mole of the diacyl bromide per mole of the cephalosporin sulfoxide. In contrast, and as noted above, at least 2 moles of a monocarboxylic acid bromide are required per mole of cephalosporin sulfoxide.

As mentioned above, the reduction of a cephalosporin sulfoxide with the acyl bromide is preferably carried out in the presence of a bromine scavenger. The term "bromine scavenger" as used herein refers to organic substances which react readily with bromine. For example, the bromine scavenger can be an alkene, a cycloalkene, a diene, a cyclodiene, an alkyne, a bicycloalkene, or a substituted aromatic hydrocarbon which readily undergoes electrophilic substitution with bromine, for example, the monohydric phenols and the ethers and esters of monohydric and polyhydric phenols, or the bromine scavenger can be an organo phosphite which is capable of complexing with bromine and thus effectively inactivates the bromine from further reaction. Examples of such bromine scavengers include the $C_2$ to $C_{10}$ alkenes, such as ethylene, propylene, butene-1, butene-2, isobutylene, pentene-1, pentene-2, 2-methylbutene-1, 3-methylbutene-1, hexene-1, heptene-1, octene-1, the isomeric nonenes, and the like; cycloalkenes having from 5 to 8 ring carbon atoms such as cyclopentene, cyclohexene, cycloheptene, and cyclooctene; $C_4-C_8$ dienes and cyclodienes having from 5–8 ring carbon atoms, for example, pentadiene, hexadiene, heptadiene, cyclopentadiene, cyclohexadiene, cyclooctadiene, 2,3-dimethylbutadiene-1,3, isoprene, and the like; alkynes having from 2–8 carbon atoms, such as acetylene, methylacetylene, ethylacetylene, dimethylacetylene, pentyne-1, pentyne-2, the isomeric hexynes, 3-methylbutyne-1, 3,3-dimethylbutyne-1, the isomeric octynes; substituted acetylenes, for example, methyl propiolate and propyl propiolate, and the tertiary acetylenic carbinols such as dimethylethynyl carbinol, cyclohexylethynyl carbinol, cyclopentylethynyl carbinol, and like acetylenes wherein the acetylenic bond will rapidly add bromine; bicyclic unsaturated hydrocarbons such as pinene and camphene; the phenols, substituted phenols and the lower alkyl ether and lower alkanoyl ester derivatives thereof represented by the formula

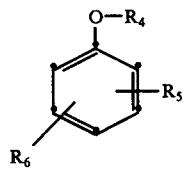

wherein $R_4$ is hydrogen, $C_1-C_4$ alkyl or $C_2-C_5$ alkanoyl, $R_5$ and $R_6$ are independently hydrogen, $C_1-C_4$ alkoxy, $C_2-C_5$ alkanoyl, or $C_1-C_4$ alkyl. Examples of such phenols and derivatives thereof include phenol, the cresols, hydroquinone monomethyl ether, hydroquinone dimethyl ether, anisole, phenetole, m-dimethoxybenzene, veratrole, guaicol, anol, eugenol, phenyl propionate, phenyl acetate, resorcinol diacetate, and like phenols and ethers and esters thereof which react readily with bromine; organophosphites such as the triaryl phosphites and tri-lower alkyl phosphites and mixed aryl alkyl phosphites such as triphenyl phosphite, tricresyl phosphite, tritolyl phosphite, trimethyl phosphite, triethyl phosphite, diphenyl ethyl phosphite, phenyl diethyl phosphite, and the like.

Among other bromine scavengers which may be mentioned include, for example, styrene, 1,1-diphenylethylene, 1,2-diphenylethylene, diphenylacetylene, and allyl benzene.

It will be recognized from an appreciation of the foregoing description of the acyl bromides and bromine scavengers, that the acyl bromide employed as a reducing agent may itself also incorporate the features of the bromine scavenger. For example, an unsaturated carboxylic acid bromide such as crotonyl bromide or the acid bromide of an acetylenic carboxylic acid such as propiolic acid may serve as both a reducing agent and the bromine scavenger by virtue of their unsaturation.

In carrying out the process of this invention, a cephalosporin sulfoxide is dissolved or suspended in an inert solvent, the bromine scavenger is added to the solution or suspension followed by the addition of the acyl bromide. The acyl bromide, if a liquid, can be added neat or, alternatively, in solution in an inert solvent. The reaction mixture is agitated, for example, with stirring until the reduction is complete. The course of the reduction can be followed by thin layer chromatography. For example, a small portion of the reaction mixture can be removed from time to time and a comparative thin layer chromatogram run with starting material and product.

As discussed above, the process of this invention is broadly applicable to the reduction of cephalosporin sulfoxides. The methods for the preparation of cephalosporin sulfoxides are well known in the art. For example, the preparation of sulfoxides can be carried out with peracids such as peracetic acid, perbenzoic acid, and especially m-chloroperbenzoic acid. Also, inorganic oxidants have been employed, for example, sodium meta periodate or hydrogen peroxide.

The following structural formula III represents a preferred group of cephalosporin sulfoxides which can be reduced to the corresponding cephalosporin.

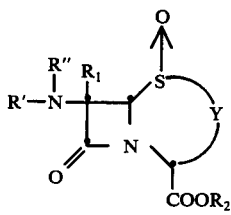

III wherein Y is

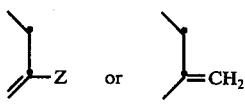

wherein Z is hydrogen, halogen, formyl, carboxy, $C_1$-$C_4$ alkoxycarbonyl, $C_1$-$C_4$ alkoxy, $C_1$-$C_4$ alkyl, phenyl, hydroxy, $C_1$-$C_4$ alkylsulfonyloxy, phenylsulfonyloxy, substituted phenylsulfonyloxy substituted by halogen or $C_1$-$C_4$-lower alkyl; vinyl, or a substituted vinyl group of the formula

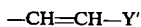

wherein Y' is $C_1$-$C_4$ alkoxycarbonyl, carboxy, cyano, diphenylmethoxycarbonyl, or phenyl,
or Z is a substituted methyl group of the formula

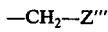

wherein Z''' is halogen, hydroxy, carbamoyloxy, $C_2$-$C_5$ alkanoyloxy, $C_1$-$C_4$ alkylthio, $C_1$-$C_4$ alkoxy, or a heterocyclic-thio group selected from among the group consisting of

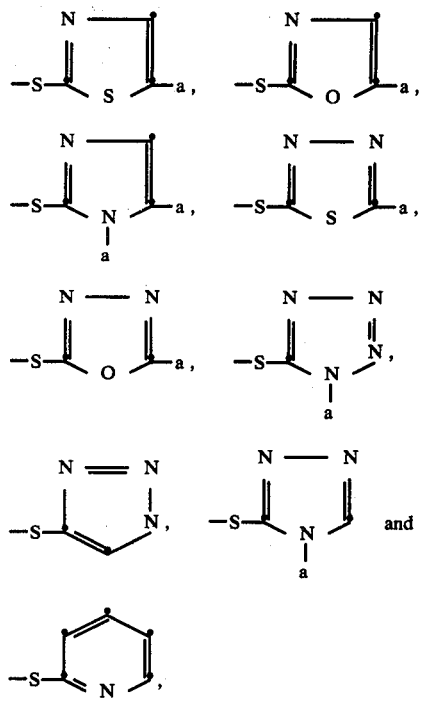

wherein $a$ is hydrogen or $C_1$-$C_4$ alkyl.
R' is formyl, $C_2$-$C_6$ alkanoyl, cyanoacetyl, bromoacetyl, benzoyl, or an acyl group of the formula

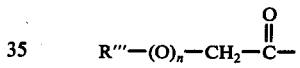

wherein R''' is phenyl, thienyl, furyl, or tetrazolyl; $n$ is 0 or 1; and when $n$ is 1, R''' is phenyl; or R' is a substituted acyl group of the formula

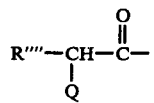

wherein R'''' is phenyl, thienyl, or furyl; Q is hydroxy, formyloxy, $C_2$-$C_4$ acyloxy, carboxy, amino, or amino substituted by t-butyloxycarbonyl, trichloroethoxycarbonyl, benzyloxycarbonyl, or p-nitrobenzyloxycarbonyl;
R'' is hydrogen or R' and R'' taken together with the nitrogen atom to which they are attached are succinimido or phthalimido;
$R_1$ is hydrogen or $C_1$-$C_4$ alkoxy; and
$R_2$ is hydrogen or a carboxylic acid protecting group.

In the above formula III the term "halogen" refers to fluoro, chloro, bromo, or iodo and preferably chloro or bromo; "$C_1$-$C_4$alkyl" refers to the straight or branched chain lower alkyl hydrocarbon groups such as methyl, ethyl, n-propyl, iso-propyl, n-butyl, sec-butyl, iso-butyl, t-butyl; "$C_1$-$C_4$ alkoxy" refers to methoxy, ethoxy, n-propoxy, n-butoxy, iso-propoxy, t-butoxy, and the like; "$C_1$-$C_4$ alkylthio" refers to methylthio, ethylthio, n-propylthio, n-butylthio, iso-propylthio, iso-butylthio, and like alkylthio groups; and "$C_1$-$C_4$ alkylsulfonyloxy" refers to methylsulfonyloxy, ethylsulfonyloxy, n-propylsulfonyloxy, and the like.

As used herein, the term "carboxylic acid protecting group" refers to those groups represented by $R_2$ in the above formula which function to protect or block the carboxylic acid function of the cephalosporin sulfoxide. For example, $R_2$ can be t-butyl, benzyl, a substituted benzyl group such as p-nitrobenzyl, p-methoxybenzyl, 3,5-dimethoxybenzyl, diphenylmethyl, 4-methoxydiphenylmethyl, 3,5-di-t-butyl-4-hydroxybenzyl, 2,2,2-trichloroethyl, 2,2,2-tribromoethyl, methoxymethyl, iodomethyl, tetrahydropyranyl, and phthalimidomethyl. Other carboxylic acid protecting groups are recognized in the cephalosporin art and such can be employed as protecting groups in the process of this invention.

The cephalosporin sulfoxide employed in the process of this invention need not be in the esterified form. For example, when $R_2$ in the above formula is hydrogen, the reduction is carried out in the manner described above.

Illustrative of the compounds described above which can be employed in the process of this invention include the sulfoxides of the following cephalosporins:

p-nitrobenzyl 7-acetamido-3-chloro-3-cephem-4-carboxylate,
p-methoxybenzyl 7-[2-(2-thienyl)acetamido]-3-bromo-3-cephem-4-carboxylate,
diphenylmethyl 7-cyanoacetyl-3-chloro-3-cephem-4-carboxylate,
p-nitrobenzyl 7-(2-t-butyloxycarbamido-2-phenylacetamido)-3-chloro-3-cephem-4-carboxylate,
diphenylmethyl 7-phenoxyacetamido-3-hydroxy-3-cephem-4-carboxylate,
diphenylmethyl 7-phenoxyacetamido-3-methoxy-3-cephem-4-carboxylate,
7-phenylacetamido-3-ethoxy-3-cephem-4-carboxylate,
diphenylmethyl 7-(2-t-butyloxycarbamido-2-phenylacetamido)-3H-3-cephem-4-carboxylate,
diphenylmethyl 7-[2-(2-thienyl)acetamido]-3-vinyl-3-cephem-4-carboxylate,
diphenylmethyl 7-(2-t-butyloxycarbamido-2-phenylacetamido)-3-vinyl-3-cephem-4-carboxylate,
p-nitrobenzyl 7-phenoxyacetamido-3-methylsulfonyloxy-3-cephem-4-carboxylate,
7-phenylacetamido-3-(p-methylphenylsulfonyloxy)-3-cephem-4-carboxylic acid,
t-butyl 7-(2-carboxy-2-phenylacetamido)-3-(2'-t-butyloxycarbonylvinyl)-3-cephem-4-carboxylate,
diphenylmethyl 7-[2-(2-thienyl)acetamido]-3-(2'-ethoxycarbonylvinyl)-3-cephem-4-carboxylate,
7-formamido-3-formyl-3-cephem-4-carboxylic acid,
p-nitrobenzyl 7-[2-(2-furyl)acetamido]-3-methyl-3-cephem-4-carboxylate,
diphenylmethyl 7-formamido-3-bromomethyl-3-cephem-4-carboxylate,
3,5-dimethoxybenzyl 7-phenylacetamido-3-bromomethyl-3-cephem-4-carboxylate,
2,2,2-trichloroethyl 7-acetamido-3-hydroxymethyl-3-cephem-4-carboxylate,
7-formamido-3-(1-methyl-1H-tetrazole-5-ylthiomethyl)-3-cephem-4-carboxylic acid,
p-nitrobenzyl 7-mandelamido-3-(1-methyl-1H-tetrazole-5-ylthiomethyl)-3-cephem-4-carboxylate,
p-nitrobenzyl 7-(2-formyloxy-2-phenylacetamido)-3-(1-methyl-1H-tetrazole-5-ylthiomethyl)-3-cephem-4-carboxylate,
7-tetrazoleacetamido-3-(5-methyl-1,3,4-thiadiazole-2-ylthiomethyl)-3-cephem-4-carboxylic acid,
p-nitrobenzyl 7-phenoxyacetamido-3-methyl-3-cephem-4-carboxylate,
p-nitrobenzyl 7-phenoxyacetamido-3-exomethylenecepham-4-carboxylate,
2,2,2-trichloroethyl 7-phenylacetamido-3-exomethylenecepham-4-carboxylate,
p-methoxybenzyl 7-formamido-3-exomethylenecepham-4-carboxylate,
benzyl 7-[2-(2-thienyl)acetamido]-3-hydroxymethyl-3-cephem-4-carboxylate,
benzyl 7-benzamido-3-acetoxymethyl-3-cephem-4-carboxylate,
7-[2-(2-thienyl)acetamido]-3-methyl-3-cephem-4-carboxylic acid,
7-[2-(2-furyl)acetamido]-3-acetoxymethyl-3-cephem-4-carboxylic acid,
p-nitrobenzyl 7-[2-(2-thienyl)acetamido]-3-acetoxymethyl-3-cephem-4-carboxylate,
p-nitrobenzyl 7-[2-(2-thienyl)acetamido]-3-carbamoyloxymethyl-3-cephem-4-carboxylate,
diphenylmethyl 7-[2-(2-thienyl)acetamido]-7-methoxy-3-carbamoyloxymethyl-3-cephem-4-carboxylate,
p-nitrobenzyl 7[2-(2-thienyl)acetamido]-7-methoxy-3-exomethylenecepham-4-carboxylic acid,
diphenylmethyl 7-[2-(2-thienyl)acetamido]-3-ethoxycarbonyl-3-cephem-4carboxylate, and
diphenylmethyl 7-phthalimido-3-bromomethyl-3-cephem-4-carboxylate.

Especially preferred cephalosporin sulfoxides which can be reduced by the process of this invention are represented by the above structural formula III wherein R" and $R_1$ are both hydrogen and Y is

Examples of these preferred compounds are listed below, wherein $R_2$ is hydrogen or the indicated ester.

| R' | Z | $R_2$ |
|---|---|---|
| phenylacetyl | —CH₃ | pNB[1] |
| " | —CH₂Br | " |
| " | —CH₂OC(O)—CH₃ | " |
| " | —OH | " |
| " | —Cl | " |
| " | —C(O)—H (formyl) | " |
| phenoxyacetyl | —CH₃ | " |
| " | " | DPM[2] |
| " | —CH₂Br | " |
| " | —CH₂—O—C(O)—CH₃ | " |
| " | —OH | pNB |
| " | —Cl | " |
| " | —Br | " |
| " | —C(O)—H (formyl) | " |
| " | —CH₂OH | " |
| 2-thienylacetyl | —CH₃ | benzyl |
| " | " | pNB |
| " | " | DPM |
| " | " | TCE[3] |
| " | —CH₂Br | pNB |
| " | —CH₂OH | " |
| " | —CH₂O—C(O)—CH₃ | " |
| " | Cl | " |
| " | Br | " |
| " | —OH | " |

-continued

| R' | | R₂ |
|---|---|---|
| formyl | —C(=O)—H (formyl)<br>—CH₃<br>—CH₂OH<br>—CH₂Br | TCE<br>DPM<br>"<br>" |
| " | —CH₂O—C(=O)—CH₃<br>—OH | pNB<br>" |
| " | —C(=O)—H (formyl) | " | and wherein Y is $\rangle\!=\!CH_2$,

| R' | R₂ |
|---|---|
| formyl | DPM |
| " | pNB |
| " | TCE |
| acetyl | pNB |
| phenylacetyl | " |
| " | DPM |
| " | TCE |
| " | pMB⁴ |
| phenoxyacetyl | pNB |
| " | DPM |
| " | TCE |
| 2-thienylacetyl | " |
| " | pNB |
| " | DPM |

¹p-nitrobenzyl
²diphenylmethyl (benzhydryl)
³2,2,2-trichloroethyl
⁴p-methoxybenzyl Examples of these preferred compounds are:

p-nitrobenzyl 7-phenylacetamido-3-methyl-3-cephem-4-carboxylate,
p-nitrobenzyl 7-acetamido-3-bromomethyl-3-cephem-4-carboxylate,
p-nitrobenzyl 7-phenylacetamido-3-acetoxymethyl-3-cephem-4-carboxylate,
p-nitrobenzyl 7-phenylacetamido-3-exomethylenecepham-4-carboxylate,
diphenylmethyl 7-phenoxyacetamido-3-methyl-3-cephem-4-carboxylate,
p-nitrobenzyl 7-phenoxyacetamido-3-exomethylenecepham-4-carboxylate,
diphenylmethyl 7-phenoxyacetamido-3-bromomethyl-3-cephem-4-carboxylate,
benzyl 7-[2-(thienyl)acetamido]-3-exomethylenecepham-4-carboxylate,
p-nitrobenzyl 7-[2-(2-thienyl)acetamido]-3-exomethylenecepham-4-carboxylate,
p-nitrobenzyl 7-[2-(2-thienyl)acetamido]-3-bromomethyl-3-cephem-4-carboxylate,
diphenylmethyl 7-formamido-3-exomethylenecepham-4-carboxylate, and
p-nitrobenzyl 7-formamido-3-bromomethyl-3-cephem-4-carboxylate.

Whereas the reduction of a cephalosporin sulfoxide by the process of this invention can be carried out under the conditions described above, certain conditions and reagents are preferred. Acetyl bromide, because of its ready availability, is the preferred acyl bromide reducing agent, and the preferred bromine scavenger is an alkene and preferably a $C_2$–$C_5$ alkene such as ethylene, propylene, butylene or amylene. A number of commonly employed organic solvents can be used in the process of this invention; however, methylene chloride, tetrahydrofuran, and acetonitrile or mixtures thereof have the widest applicability in the process of this invention.

To illustrate the use of different solvents in the process of this invention p-nitrobenzyl 7-phenoxyacetamido-3-exomethylenecepham-4-carboxylate sulfoxide was reduced with acetyl bromide in the presence of amylene at a temperature of 0° C. in different solvents, the product isolated, and the yield calculated. The product was isolated by evaporating the reduction mixture to dryness in vacuo and the reduction product obtained crystalline with absolute alcohol. The product was dried in vacuo before weighing. The percent yield of product for the indicated solvents is shown below.

| Solvent | Percent Yield¹ |
|---|---|
| acetonitrile | 84.3 |
| tetrahydrofuran | 61.2 |
| acetone | 78.5 |
| chloroform | 87.6 |
| methylene chloride | 93.8 |

¹additional unrecovered product was present in the filtrate.

As previously discussed, the process of this invention is preferably carried out in the presence of a bromine scavenger. To illustrate the variety of bromine scavengers which can be used a series of reductions of p-nitrobenzyl 7-phenoxyacetamido-3-exomethylenecepham sulfoxide were carried out with acetyl bromide in methylene chloride at a temperature of 0° C. In each reduction a different bromine scavenger was employed and the percent yield of the isolated, dried product calculated. The yield obtained with the respective bromine scavengers is listed below.

| Br₂ Scavenger | Percent Yield¹ |
|---|---|
| 1-octene | 81.6 |
| cyclooctene | 85.3 |
| camphene | 84.9 |
| cyclohexene | 81.2 |
| cyclopentene | 80.8 |
| cycloheptene | 83.9 |
| 1-hexene | 81.8 |
| phenylacetylene | 59.7 |
| m-dimethoxybenzene | 58.3 |

¹Additional unrecovered product was present in the filtrate.

The sulfoxides employed in the process have been previously described, for example, in the numerous U.S. patents previously cited herein. With reference to the above formula III, the compounds wherein Z is carboxy or $C_1$–$C_4$ alkoxycarbonyl are described by Spry in U.S. Pat. No. 3,953,346 issued Apr. 27, 1976. The 3-hydroxy-3-cephem sulfoxides and 3-exomethylenecepham sulfoxides are described by Chauvette in U.S. Pat. No. 3,917,587 issued Nov. 4, 1975. The 3-vinyl and 3-substituted-vinyl-3-cephem compounds (Z = —CH=CH₂ or —CH=CH—Y') are taught in U.S. Pat. No. 3,769,277. Further, Cooper describes a generally applicable method for the synthesis of cephalosporin sulfoxides in U.S. Pat. No. 3,647,686.

The products of the process described herein are known antibiotic compounds or are intermediates useful in the preparation of antibiotics. For example, when in the above formulas R₂ is an ester group, the ester group is removed after the process to provide the antibiotic free acid. Likewise, amino-protecting groups represented by R' in the formula III, for example, the t-butyloxycarbonyl group, can be removed to provide the reduced free 7-amino nucleus compound. The 7- amino nucleus compound is then acylated with a suitable active derivative of a carboxylic acid, such as the acid chloride of thiophene-2-acetic acid, to provide the antibiotic compound.

The 3-exomethylenecepham sulfoxides which are starting materials in a preferred embodiment of this invention are prepared as described by S. Kukolja in copending application Ser. No. 673,036, filed Apr. 2, 1976. By this method, a penicillin sulfoxide ester is converted to a 3-exomethylenecepham sulfoxide ester as illustrated with penicillin V sulfoxide p-nitrobenzyl ester. Initially, p-nitrobenzyl 6-phenoxyacetamidopenicillanate sulfoxide is reacted with an N-halo imide such as N-bromosuccinimide (NBS) to provide the ring opened azetidinone-2 sulfinyl halide ester. The sulfinyl chloride ester is then reacted in an inert solvent with a Lewis Acid-Friedel-Crafts catalyst such as stannic chloride to provide p-nitrobenzyl 7-phenoxyacetamido-3-exomethylenecepham-4-carboxylate sulfoxide. The above synthesis is illustrated by the following scheme.

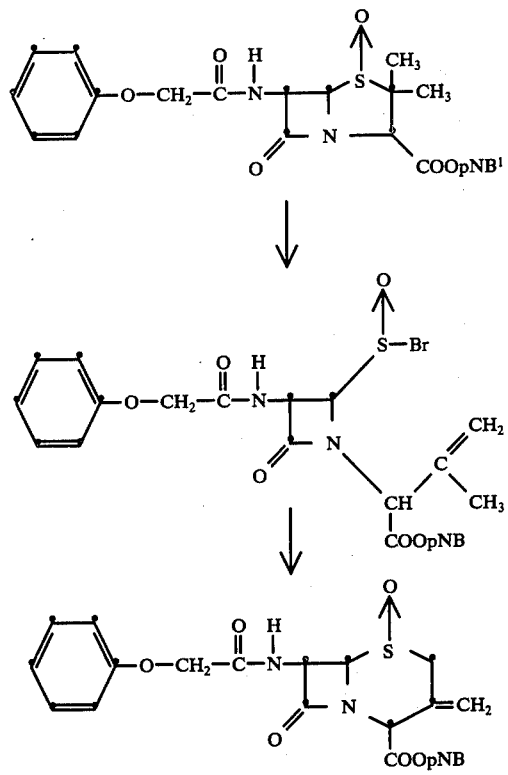

¹pNB = p-nitrobenzyl

The product, 3-exomethylenecepham sulfoxide ester is useful in the preparation of 3-substituted-methyl cephalosporin antibiotics. For example, the 3-exomethylenecepham sulfoxide is reduced via the process of this invention, to the corresponding sulfide exomethylene ester and is converted to the 3-bromomethyl 3-cephem ester. The 3-bromomethyl ester can then be reacted with an appropriate alcohol, thiol, or amine to obtain, via nucleophilic displacement of the bromo group, the desired substituent. For example, the 3-bromomethyl 3-cephem ester can be reacted with 5-methyl-1,3,4-thiadiazole-2-thiol or 1-methyl-1H-tetrazole-5-thiol to prepare the corresponding 7-acylamido-3-heterocyclicthiomethyl-3-cephem-4-carboxylic acid.

The conversion of the 3-exomethylenecepham ester to the 3-bromomethyl-3-cephem ester is carried out as described by Koppel in copending application Ser. No. 669,365 filed Mar. 22, 1976.

According to the described method, the 3-exomethylenecepham ester is reacted in an inert solvent with 1,5-diazabicyclo[5.4.0]undec-5-ene, "DBU" in the presence of bromine to form the 3-bromomethyl-3-cephem ester.

Alternatively, a 3-exomethylenecepham sulfoxide ester can be converted via the above-described process to the 3-bromomethyl-3-cephem sulfoxide ester and the latter reduced in the process of this invention. In a further alternative, the 3-bromomethyl-3-cephem sulfoxide ester can be reacted with a thiol, e.g., 1-methyl-1H-tetrazole-5-thiol and then the product 3-(1-methyl-1H-tetrazole-5-thiomethyl)-3-cephem sulfoxide ester reduced in the process of this invention.

The foregoing process is illustrated by the following scheme:

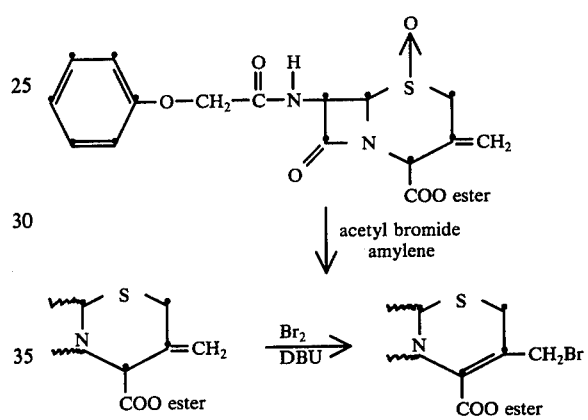

Cephalosporin sulfoxides are also useful in isolating and purifying cephalosporin antibiotics and intermediates thereto. The cephalosporin in the sulfoxide form is generally more polar than the corresponding sulfide form and is more readily purified. Accordingly, the cephalosporin antibiotic or intermediate, e.g., an ester thereof, can be converted to the sulfoxide, purified by chromatography, and then the purified sulfoxide reduced via the process of this invention.

The cephalosporin sulfoxides represented by the formula III wherein Z is a $C_1$-$C_4$ alkylsulfonyloxy group or a phenyl or substituted phenylsulfonyloxy group are prepared by the method disclosed in copending application Ser. No. 439,207, filed Feb. 6, 1974 now U.S. Pat. No. 3,985,737. These cephalosporin 3-sulfonate esters are prepared by reacting in an aprotic solvent a 7-acylamido-3-hydroxy-3-cephem ester with an alkyl or phenysulfonyl halide in the presence of a hydrogen halide acceptor. For example, 7-[2-(2-thienyl)acetamido]-3-hydroxy-3-cephem-4-carboxylic acid p-nitrobenzyl ester is reacted in DMF with methanesulfonyl chloride in the presence of propylene oxide to provide p-nitrobenzyl 7-[2-(2-thienyl)-acetamido]-3-methylsulfonyloxy-3-cephem-4-carboxylate. The 3-hydroxy-3-cephem ester sulfoxides will likewise form the 3-sulfonyloxy-3-cephem ester sulfoxides which are reduced via the process of this invention.

The sulfoxide reduction process of this invention is further illustrated by the following examples.

The products obtained in the following examples were identified by thin layer chromatographic comparison with authentic materials and in many instances by their nuclear magnetic resonance spectrum.

EXAMPLE 1

To a suspension of 2.50 g. (5 mM) of p-nitrobenzyl 7-phenoxyacetamido-3-methyl3-cephem-4-carboxylate sulfoxide in 25 ml. of methylene chloride containing approximately 1 ml. of 2-methyl-2-butene was added 0.9 ml. (12 mM) of acetyl bromide. The mixture was stirred for 1.5 hours at room temperature. After approximately 40 minutes, a clear solution was obtained. The reaction solution was evaporated in vacuo to remove the methylene chloride leaving the product as an off-white solid residue. The product was triturated with 25 ml. of methanol, was filtered and washed on the filter with methanol. The product was dried to yield 2.30 g. (95.0 percent yield) of the product, p-nitrobenzyl 7-phenoxyacetamido-3-methyl-3-cephem-4-carboxylate.

EXAMPLE 2

To a suspension of 5.2 g. (10 mM) of p-nitrobenzyl 7-phenoxyacetamido-3-chloro-3-cephem-4-carboxylate sulfoxide in 100 ml. of methylene chloride containing approximately 2 ml. of 2-methyl-2-butene were added 1.6 ml. (22 mM) of acetyl bromide. The reaction mixture exhibited a slight exotherm over 30 minutes with stirring, the temperature rising from 20° to 22° C. After stirring for one hour at ambient temperature, a clear solution was obtained. After stirring for about 90 minutes, the reaction solution was concentrated in vacuo on a rotary evaporator to yield the product as a syrupy residue. The syrup crystallized on slow addition of 50 ml. of methanol. The suspension of the crystalline product in methanol thus obtained was stirred for 15 minutes and was then filtered and the nearly white crystals were washed on the filter with methanol and dried to yield 4.46 g. (88.5 percent yield) of p-nitrobenzyl 7-phenoxyacetamido-3-chloro-3-cephem-4-carboxylate.

EXAMPLE 3

A solution of 2.50 g. (5 mM) of p-nitrobenzyl 7-phenoxyacetamido-3-exomethylenecepham-4-carboxylate sulfoxide in 40 ml. of methylene chloride containing 1 ml. of 2-methyl-2-butene was cooled to a temperature of about 0° C. The solution was protected from atmospheric moisture with a calcium chloride drying tube. With stirring a solution of 0.9 ml. (12 mM) of acetyl bromide in 6 ml. of methylene chloride was added dropwise to the cold solution. The reaction mixture was stirred for 90 minutes at 0° C. and was evaporated under vacuum to yield the product as a solid residue. The residue was crystallized from 25 ml. of ethanol to yield 2.27 g. (93.8 percent yield) of the product, p-nitrobenzyl 7-phenoxyacetamido-3-exomethylenecepham-4-carboxylate as snow white crystals.

EXAMPLE 4

A suspension of 4.84 g. of p-nitrobenzyl 7-phenylacetamido-3-exomethylenecepham-4-carboxylate sulfoxide in 50 ml. of methylene chloride containing 2 ml. of amylene was cooled to 0° C. A solution of 1.8 ml. (24 mM) of acetyl bromide in 3 ml. of methylene chloride were added dropwise to the cold suspension. The mixture was stirred for 2 hours at 0° C. and was then warmed to 20° C. when a clear solution was obtained. The reaction solution was evaporated in vacuo and the residue crystallized with 50 ml. of methanol. The crystalline product was filtered and washed on the filter with 30 ml. of methanol and vacuum dried to yield 4.31 g. (92.1 percent yield) of p-nitrobenzyl 7-phenylacetamido-3-exomethylenecepham-4-carboxylate.

EXAMPLE 5

A solution of 10 g. of p-nitrobenzyl 7-phenoxyacetamido-3-hydroxy-3-cepham-4-carboxylate sulfoxide in 100 ml. of methylene chloride and 10 ml. of dimethylformamide containing 4 ml. of amylene was cooled to 15° C. and 3.6 ml. of acetyl bromide were added. The reaction mixture was stirred for 90 minutes while the temperature was maintained below 25° C. The reaction mixture was washed twice with 100 ml. portions of dilute hydrochloric acid and once with 100 ml. of a dilute solution of sodium chloride and was then filtered through anhydrous sodium sulfate. The filtrate was evaporated on a rotary evaporator and the residue crystallized from ethanol with seeding. The crystalline product, p-nitrobenzyl 7-phenoxyacetamido-3-hydroxy-3-cepham-4-carboxylate, was filtered, washed with ethanol, and dried under vacuum. The yield of dried product was 7.17 g. (73.8 percent yield).

The filtrate of the above crystallization yielded an additional 0.35 g. of crystalline product on standing.

EXAMPLE 6

To a solution of 0.557 g. of p-nitrobenzyl 7-phenoxyacetamido-3-acetoxymethyl-3-cepham-4-carboxylate sulfoxide in 25 ml. of methylene chloride cooled to 0° C. were added 2 ml. of amylene and next 0.18 ml. of acetyl bromide. The reaction mixture was stirred at 0° C. for 2 hours and was then evaporated under vacuum to yield the product as a residual gum. The product was dissolved in ethyl acetate-tetrahydrofuran (3:1, v:v) and the solution washed with dilute solution of sodium bicarbonate, water, and a dilute solution of sodium chloride. The washed solution was evaporated to dryness to yield the product as a residual gum. Attempts to crystallize the product with isopropyl acetate, isopropanol, and methanol were unsuccessful. The nuclear magnetic resonance spectrum of the reaction product was in agreement with the proposed sulfoxide reduction product, p-nitrobenzyl 7-phenoxyacetamido-3-acetoxymethyl-3-cepham-4-carboxylate.

EXAMPLE 7

To a suspension of 580 mg. of p-nitrobenzyl 7-phenoxyacetamido-3-methylsulfonyloxy-3-cepham-4-carboxylate sulfoxide in 7 ml. of methylene chloride were added dropwise over one minute 0.25 ml. of amylene and 0.185 ml. of acetyl bromide. The reaction mixture was stirred at room temperature for one hour and an additional 0.25 ml. of amylene and 0.185 ml. of acetyl bromide were added. After stirring for 10 more minutes a clear solution was obtained. The reaction mixture was stirred for 2 additional hours and was treated with charcoal and filtered. The filtered reaction mixture was diluted with isopropanol and was concentrated under reduced pressure. On standing the concentrate deposited 523.8 mg. of the product, p-nitrobenzyl 7-phenoxyacetamido-3-methylsulfonyloxy-3-cepham-4-carboxylate.

EXAMPLE 8

A solution of 5.0 g. (10 mM) of p-nitrobenzyl 7-phenoxyacetamido-3-exomethylenecepham-4-carboxylate sulfoxide in 80 ml. of methylene chloride containing 2 ml. of amylene was cooled to 0° C. and 3.29 g. (24 mM) of propionyl bromide were added. The reaction mixture was stirred for 90 minutes after which time all of the starting material had reacted as shown by a thin layer chromatogram run on a small portion of the reaction mixture.

The reaction mixture was filtered through a Filter-Aid and the filtrate evaporated on a rotary evaporator. The residue was treated with absolute ethanol to crystallize the product, p-nitrobenzyl 7-phenoxyacetamido-3-exomethylenecepham-4-carboxylate. The crystalline product was filtered, washed with alcohol and dried under vacuum. There were obtained 4.43 g. of the crystalline product (91.5% percent yield).

EXAMPLE 9

The reduction described in Example 8 was repeated except that 4.44 g. (24 mM) of benzoyl bromide were substituted for the propionyl bromide. After stirring the reaction mixture for 90 minutes at 0° C., approximately 50 percent of the starting material was unreacted as shown by a thin layer chromatogram of a small portion of the reaction mixture. The reaction mixture was allowed to warm to room temperature and was stirred for about 18 hours during which time all of the starting material had reacted. The reduction product was recovered from the reaction mixture and crystallized as described in Example 8 and 3.24 g. (66.9 percent yield) of crystalline product was obtained.

EXAMPLE 10

The reduction described by Example 8 was repeated again with the exception that 4.85 g. (24 mM) of bromoacetyl bromide were substituted for propionyl bromide. After 90 minutes reaction time at 0° C., there was obtained 1.89 g. (39.0 percent yield) of the crystalline product.

EXAMPLE 11

The reaction described by Example 8 was repeated except that 2-bromopropionyl was substituted for propionyl bromide. A mixture of 5.4 g. (25 mM) of 2-bromopropionyl bromide in 10 ml. of methylene chloride was rapidly added dropwise to the cold reaction mixture. The mixture was stirred in the cold at 0° C. for 90 minutes and 3.58 g. (74.0 percent yield) of the crystalline product was obtained by the recovery and crystallization procedures described by Example 8.

EXAMPLE 12

A solution of 5.0 g. (0.01 mM) of t-butyl 7-phenoxyacetamido-3-(2'-ethoxycarbonylvinyl)-3-cepham-4-carboxylate sulfoxide in 100 ml. of tetrahydrofuran containing 3 ml. of amylene was cooled to 0° C. and 2.8 g. of acetyl bromide are added. The reaction mixture was stirred for 2 hours in the cold and was then evaporated to dryness. The product, t-butyl 7-phenoxyacetamido-3-(2'-ethoxycarbonylvinyl)-3-cepham-4-carboxylate, was obtained crystalline with ethanol.

Alternatively, the reduced ester was converted with 98 percent formic acid at room temperature to the free acid, 7-phenoxyacetamido-3-(2-ethoxycarbonylvinyl)-3-cephem-4-carboxylic acid, and the latter obtained crystalline.

EXAMPLE 13

The following is an example of the process of this invention wherein a cephalosporin sulfoxide as the free acid is reduced.

To a solution of 0.68 g. (1.87 mM) of 7-phenoxyacetamido-3-methyl-3-cephem-4-carboxylic acid sulfoxide in 8 ml. of methylene chloride and 2 ml. of dimethylformamide was added 0.5 ml. of amylene followed by 0.31 ml. of acetyl bromide. The reaction mixture was stirred at room temperature for 90 minutes after which time a thin layer chromatogram of a small aliquot of the reaction mixture showed that all of the starting material have been converted to product. The reaction mixture was evaporated under vacuum and the residue was crystallized from 10 ml. of ethanol. There was obtained 0.42 g. (65 percent yield) of 7-phenoxyacetamido-3-methyl-3-cephem-4-carboxylic acid. The product was confirmed by its nuclear magnetic resonance spectrum and a comparative thin layer chromatogram with authentic material.

Additional product was present in the filtrate from the crystallization but was not recovered.

I claim:

1. The process for reducing a cephalosporin sulfoxide to the corresponding cephalosporin which comprises reacting said sulfoxide in an inert solvent at a temperature between $-25°$ C. and about 50° C. with at least 2 molar equivalents per mole of sulfoxide of an acyl bromide of the formula

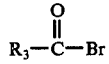

wherein $R_3$ is $C_1$-$C_{10}$ alkyl; $C_1$-$C_{10}$ alkyl substituted by halogen, cyano, phenyl, $C_1$-$C_4$ alkoxy, or $C_1$-$C_4$ alkoxycarbonyl; phenyl, or phenyl substituted by halogen, cyano, nitro, $C_1$-$C_4$ alkyl, $C_1$-$C_4$ alkoxy, or $C_1$-$C_4$ alkoxycarbonyl; or $R_3$ is a cycloalkyl group having from 3 to 8 ring carbon atoms; in the presence of a bromine scavenger wherein said sulfoxide is a 3-cephem sulfoxide or a 3-exomethylenecepham sulfoxide.

2. The process of claim 1 wherein $R_3$ is $C_1$-$C_{10}$ alkyl.

3. The process of claim 2 wherein $R_3$ is methyl.

4. The process of claim 1 wherein the bromine scavenger is a $C_2$-$C_{10}$ alkene, a cycloalkene having from 5-8 ring carbon atoms, a cyclodiene having from 5-8 ring carbon atoms, a $C_4$-$C_8$ alkadiene, a $C_2$-$C_8$ alkyne; a $C_2$-$C_8$ alkyne substituted by lower alkoxycarbonyl, a $C_3$-$C_8$ alkyne substituted by hydroxy or a readily brominated phenol or derivative thereof of the formula

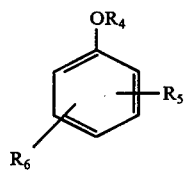

wherein $R_4$ is hydrogen, $C_1$-$C_4$ alkyl, or $C_2$-$C_5$ alkanoyl, $R_5$ and $R_6$ are independently hydrogen, $C_1$-$C_4$ alkoxy, $C_2$-$C_5$ alkanoyl or $C_1$-$C_4$ alkyl; or said bromine scavenger is a tri($C_1$-$C_4$ alkyl)phosphite, triphenyl phosphite, a substituted triphenyl phosphite wherein one or more of the phenyl groups are substituted by $C_1$-$C_4$ lower alkyl, or a mixed tri($C_1$-$C_4$ alkyl), phenyl, or lower alkyl substituted phenyl phosphite.

5. The process of claim 4 wherein the bromine scavenger is a $C_2$-$C_5$ alkene.

6. The process of claim 5 wherein the alkene is ethylene, propylene, or amylene.

7. The process of claim 1 wherein the cephalosporin sulfoxide is a compound of the formula

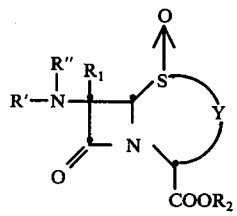
III wherein Y is

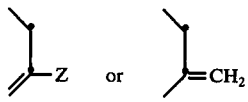

wherein Z is hydrogen, halogen, formyl, carboxy, $C_1$-$C_4$ alkoxycarbonyl, $C_1$-$C_4$ alkoxy, $C_1$-$C_4$ alkyl, phenyl, hydroxy, $C_1$-$C_4$ alkylsulfonyloxy, phenylsulfonyloxy, substituted phenylsulfonyloxy substituted by halogen or $C_1$-$C_4$ lower alkyl, vinyl, or a substituted vinyl group of the formula

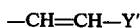

wherein Y' is $C_1$-$C_4$ alkoxycarbonyl, carboxy, cyano, diphenylmethoxycarbonyl, or phenyl, or Z is a substituted methyl group of the formula

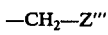

wherein Z''' is halogen, hydroxy, carbamoyloxy, $C_2$-$C_5$ alkanoyloxy, $C_1$-$C_4$ alkylthio, $C_1$-$C_4$ alkoxy, or a heterocyclic-thio group selected from among the group consisting of

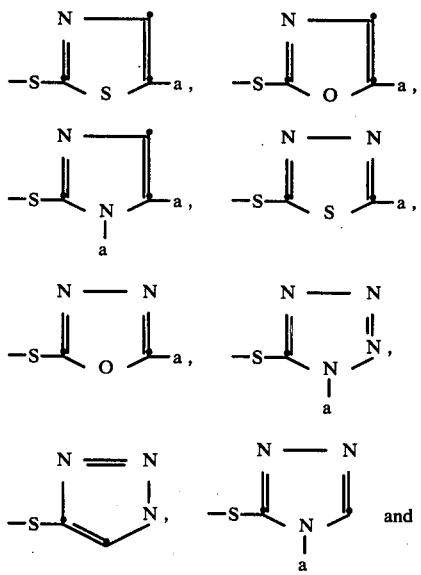

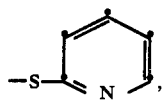

wherein a is hydrogen or $C_1$-$C_4$ alkyl.

R' is formyl, $C_2$-$C_6$ alkanoyl, cyanoacetyl, bromoacetyl, benzoyl, or an acyl group of the formula

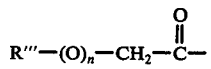

wherein R''' is phenyl, thienyl, furyl, or tetrazolyl; $n$ is 0 or 1; and when $n$ is 1, R''' is phenyl; or R' is a substituted acyl group of the formula

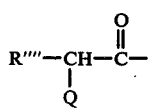

wherein R'''' is phenyl, thienyl, or furyl; Q is hydroxy, formyloxy, $C_2$-$C_4$ acyloxy, carboxy, amino, or amino substituted by t-butyloxycarbonyl, trichloroethoxycarbonyl, benzoyloxycarbonyl, or p-nitrobenzyloxycarbonyl;

R'' is hydrogen or R' and R'' taken together with the nitrogen atom to which they are attached are succinimido or phthalimido;

$R_1$ is hydrogen or $C_1$-$C_4$ alkoxy; and $R_2$ is hydrogen or a carboxylic acid protecting group.

8. The process of claim 7 wherein the acyl bromide is a $C_2$-$C_{10}$ alkyl carboxylic acid bromide and the bromine scavenger is a $C_2$-$C_5$ alkene.

9. The process of claim 7 wherein Y is

10. The process of claim 9 wherein R' is phenoxyacetyl, phenylacetyl, 2-thienylacetyl, or formyl, and wherein Z is methyl, acetoxymethyl, bromomethyl, hydroxymethyl, formyl, hydroxy, methylsulfonyloxy, chloro, or bromo.

11. The process of claim 10 wherein the acyl bromide is acetyl bromide and the bromine scavenger is a $C_2$-$C_5$ alkene.

12. The process of claim 11 wherein R' is phenoxyacetyl or phenylacetyl; Z is methyl, acetoxymethyl, bromomethyl, formyl, chloro, hydroxy, or methylsulfonyloxy.

13. The process of claim 11 wherein the sulfoxide is p-nitrobenzyl 7-phenoxyacetamido-3-methyl-3-cepham-4-carboxylate sulfoxide.

14. The process of claim 11 wherein the sulfoxide is p-nitrophenyl 7-phenoxyacetamido-3-chloro-3-cephem-4-carboxylate sulfoxide.

15. The process of claim 11 wherein the sulfoxide is p-nitrobenzyl 7-phenoxyacetamido-3-acetoxymethyl-3-cephem-4-carboxylate sulfoxide.

16. The process of claim 11 wherein the sulfoxide is p-nitrobenzyl 7-phenoxyacetamido-3-hydroxy-3-cephem-4-carboxylate sulfoxide.

17. The process of claim 11 wherein the sulfoxide is p-nitrobenzyl 7-phenoxyacetamido-3-methylsulfonyloxy-3-cephem-4-carboxylate sulfoxide.

18. The process of claim 7 wherein Y is

19. The process of claim 18 wherein R' is formyl, acetyl, phenylacetyl, phenoxyacetyl, or 2-thienylacetyl.

20. The process of claim 19 wherein the acyl bromide is acetyl bromide and the bromine scavenger is a $C_2$–$C_5$ alkene.

21. The process of claim 20 wherein R' is phenylacetyl or phenoxyacetyl and $R_2$ is a carboxylic acid protecting group.

22. The process of claim 20 wherein the sulfoxide is p-nitrobenzyl 7-phenylacetamido-3-exomethylenecepham-4-carboxylate sulfoxide.

23. The process of claim 20 wherein the sulfoxide is p-nitrobenzyl 7-phenoxyacetamido-3-exomethylenecepham-4-carboxylate sulfoxide.

* * * * *